United States Patent
Hayano

(10) Patent No.: US 10,590,233 B2
(45) Date of Patent: *Mar. 17, 2020

(54) HYDROGENATED SYNDIOTACTIC CRYSTALLINE DICYCLOPENTADIENE RING-OPENING POLYMER, SYNDIOTACTIC DICYCLOPENTADIENE RING-OPENING POLYMER, AND PRODUCTION METHOD FOR THESE

(71) Applicant: ZEON CORPORATION, Tokyo (JP)

(72) Inventor: Shigetaka Hayano, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/556,168

(22) PCT Filed: Feb. 4, 2016

(86) PCT No.: PCT/JP2016/053339
§ 371 (c)(1),
(2) Date: Sep. 6, 2017

(87) PCT Pub. No.: WO2016/143424
PCT Pub. Date: Sep. 15, 2016

(65) Prior Publication Data
US 2018/0044468 A1    Feb. 15, 2018

(30) Foreign Application Priority Data

Mar. 9, 2015    (JP) .................... 2015-046498

(51) Int. Cl.
| | | |
|---|---|---|
| *C08G 61/08* | (2006.01) | |
| *C07C 13/64* | (2006.01) | |
| *C08F 4/78* | (2006.01) | |
| *C08F 8/04* | (2006.01) | |
| *C08F 132/08* | (2006.01) | |

(52) U.S. Cl.
CPC ............. *C08G 61/08* (2013.01); *C07C 13/64* (2013.01); *C08F 4/78* (2013.01); *C08F 8/04* (2013.01); *C08F 132/08* (2013.01); *C08F 2500/16* (2013.01); *C08G 2261/212* (2013.01); *C08G 2261/3325* (2013.01); *C08G 2261/418* (2013.01); *C08G 2261/592* (2013.01); *C08G 2261/62* (2013.01); *C08G 2261/724* (2013.01)

(58) Field of Classification Search
CPC .......... C08G 61/08; C08F 132/08; C08F 8/04; C08F 4/78; C07C 13/64
See application file for complete search history.

(56) References Cited

U.S. PATENT DOCUMENTS

| | | |
|---|---|---|
| 6,511,756 B1 | 1/2003 | Obuchi et al. |
| 2007/0185290 A1 | 8/2007 | Hayano et al. |
| 2015/0240008 A1* | 8/2015 | Schrock .................. C07F 11/00 525/332.1 |
| 2016/0137794 A1 | 5/2016 | Yamada et al. |
| 2018/0051129 A1* | 2/2018 | Kato ...................... C08G 61/08 |
| 2018/0079876 A1* | 3/2018 | Kato ...................... C08G 61/08 |

FOREIGN PATENT DOCUMENTS

| | | |
|---|---|---|
| EP | 3 107 655 A1 | 12/2016 |
| JP | 2002-249554 A | 9/2002 |
| JP | 2005-89744 A | 4/2005 |
| JP | 2013-139513 A | 7/2013 |
| JP | 2014-520103 A | 8/2014 |
| JP | 2014-162811 A | 9/2014 |
| JP | 5896194 B1 | 3/2016 |
| WO | 2012/167171 A2 | 12/2012 |
| WO | 2015/127192 A1 | 8/2015 |

OTHER PUBLICATIONS

Richardson, M.J., Thermochimica Acta 300 (1997) 15-28.*
Autenrieth et al., Macromolecules 48 (2015) 2480-2492.*
International Search Report dated Mar. 15, 2016, issued in counterpart International Application No. PCT/JP2016/053339 (1 page).
Flook, Margaret M. et al., "Five-Coordinate Rearrangements of Metallacyclobutane Intermediates during Ring-Opening Metathesis Polymerization of 2,3-Dicarboalkoxynorbornenes by Molybdenum and Tungsten Monoalkoxide Pyrrolide Initiators", Organometallics, vol. 31, No. 17, Aug. 14, 2017, pp. 6231-6243.
Extended Search Report dated Nov. 16, 2018, issued in counterpart European Application No. 16761396.7 (7 pages).
Extended (Supplementary) European Search Report dated Oct. 15, 2018, issued in EP application 16761763.8 (counterpart to U.S. Appl. No. 15/553,700)(8 pages).
Non-Final Office Action dated Oct. 30, 2018, issued in U.S. Appl. No. 15/553,700 (6 pages).
Non-Final Office Action dated Sep. 10, 2018, issued in U.S. Appl. No. 15/554,279 (10 pages).

(Continued)

*Primary Examiner* — Peter D. Mulcahy
(74) *Attorney, Agent, or Firm* — Westerman, Hattori, Daniels & Adrian, LLP

(57) ABSTRACT

The present invention provides a hydrogenated syndiotactic crystalline dicyclopentadiene ring-opening polymer having a melting point of lower than 280° C., an initial melting temperature of 260° C. or higher and a syndiotacticity of higher than 90%, and a syndiotactic dicyclopentadiene ring-opening polymer, and a method for producing the syndiotactic dicyclopentadiene ring-opening polymer, and a method for producing the hydrogenated syndiotactic crystalline dicyclopentadiene ring-opening polymer. The hydrogenated syndiotactic crystalline dicyclopentadiene ring-opening polymer has a sufficiently high initial melting temperature, excellent heat resistance and advantageous industrial producibility. The syndiotactic dicyclopentadiene ring-opening polymer is excellent in solution stability after polymerization reaction and can be converted into the hydrogenated product by hydrogenation reaction.

4 Claims, No Drawings

(56) References Cited

OTHER PUBLICATIONS

International Search Report dated Jun. 7, 2016, issued in application No. PCT/JP2016/057208 (counterpart to U.S. Appl. No. 15/554,279), with English translation. (5 pages).
Autenrieth et al., Macromolecules 2015, 48, 2480-2492.

* cited by examiner

HYDROGENATED SYNDIOTACTIC CRYSTALLINE DICYCLOPENTADIENE RING-OPENING POLYMER, SYNDIOTACTIC DICYCLOPENTADIENE RING-OPENING POLYMER, AND PRODUCTION METHOD FOR THESE

TECHNICAL FIELD

The present invention relates to a hydrogenated syndiotactic crystalline dicyclopentadiene ring-opening polymer having high initial melting temperature and excellent heat resistance, a syndiotactic dicyclopentadiene ring-opening polymer that is excellent in solution stability alter polymerization reaction and can be converted to the hydrogenated product by hydrogenation reaction, and a production method thereof.

BACKGROUND ART

A hydrogenated ring-opening polymer of a norbornene-based monomer such as dicyclopentadiene is a type of so-called cycloolefin polymer that exhibits excellent transparency, low birefringence, forming processability and the like, and thus is used as a material that can be applied to various applications such as optical applications.

A hydrogenated ring-opening polymer of dicyclopentadiene is normally obtained in the form of an amorphous polymer that has an atactic structure. However, the amorphous hydrogenated ring-opening polymer of dicyclopentadiene having the atactic structure may exhibit insufficient heat resistance, mechanical strength, solvent resistance and the like depending on the application. Hence in order to improve the performance of such a hydrogenated ring-opening polymer, a hydrogenated ring-opening polymer of dicyclopentadiene that has crystallinity obtained by producing a hydrogenated ring-opening polymer of dicyclopentadiene having a tactic structure on its main chain has been proposed.

For example, Patent Literature 1 discloses that a dicyclopentadiene ring-opening polymer having cis-syndio regularity that is soluble in a hydrocarbon solvent such as a cyclohexane at room temperature is obtained by subjecting dicyclopentadiene to ring-opening polymerization using a polymerization catalyst that mainly includes a group 6 transition metal compound having a specific substituent such as a phenylimidotungsten tetrachloride diethyl ether complex, and furthermore a hydrogenated syndiotactic crystalline dicyclopentadiene ring-opening, polymer having crystallinity is obtained by hydrogenating the carbon-carbon double bonds included in the ring-opening polymer using a mixture of a bis(tricyclohexylphosphine)benzylideneruthenium(IV) dichloride and ethyl vinyl ether or the like, as a hydrogenation catalyst. In addition, Patent Literature 2 discloses that a crystalline dicyclopentadiene ring-opening polymer having cis-iso regularity that is insoluble in a hydrocarbon solvent such as cyclohexane at room temperature is obtained by subjecting dicyclopentadiene to ring-opening polymerization using a polymerization catalyst that mainly includes a group 4 to 6 transition metal compounds that include a specific aromatic dioxy group as a ligand such as a phenylimidotungsten bisphenolate complex, and a hydrogenated isotactic crystalline dicyclopentadiene ring-opening polymer having crystallinity is obtained by hydrogenating the carbon-carbon double bonds included m the ring-opening polymer using $RuHCl(CO)(PPh_3)^2$ or the like as a hydrogenation catalyst.

CITATION LIST

Patent Literature

Patent Literature 1: JP-A-2005-089744 (US2007/0185290A1)
Patent Literature 2: JP-A-2013-139513

SUMMARY OF INVENTION

Technical Problem

A review by the present inventor about the hydrogenated syndiotactic crystalline dicyclopentadiene ring-opening polymer specifically described in Patent Literature 1 indicated that this hydrogenated syndiotactic crystalline dicyclopentadiene ring-opening polymer had a melting point as high as about 270° C., but it began to soften (melt) from lower than 260° C. when the polymer was heated, and thus a substantial upper temperature limit was lower than 260° C.

Meanwhile, the hydrogenated isotactic crystalline dicyclopentadiene ring-opening polymer specifically described in Patent Literature 2, its isotaticity was 100% within the measurement accuracy for the analyzer, and, its melting point was about 295° C. which is extremely high. However, the dicyclopentadiene ring-opening polymer having a cis-isotactic structure was insoluble in a hydrocarbon solvent such as cyclohexane at room temperature, and thus the polymer was difficult to produce in an industrial production scale.

The present invention has been made under such circumstances, and an object of the present invention is to provide a hydrogenated syndiotactic crystalline dicyclopentadiene ring-opening polymer having a sufficiently high initial melting temperature, excellent heat resistance and advantageous industrial producibility, a syndiotactic dicyclopentadiene ring-opening polymer that is excellent in solution stability after polymerization reaction and can be converted into the hydrogenated product by hydrogenation reaction, and an efficient production method thereof.

Solution to Problem

As a result of extensive studies to achieve the above object, the present inventor has found that a dicyclopentadiene ring-opening polymer soluble in a hydrocarbon solvent at room temperature can be obtained by subjecting dicyclopentadiene to ring-opening polymerization using a polymerization catalyst including a tungsten compound having a particular structure, and a hydrogenated syndiotactic crystalline dicyclopentadiene ring-opening polymer having an extremely high initial melting temperature can be obtained by hydrogenating a carbon-carbon double bond included in this dicyclopentadiene ring-opening polymer. The present invention has been completed on the basis of these findings.

Thus, one aspect of the invention provides the followings: [1] a hydrogenated syndiotactic crystalline dicyclopentadiene ring-opening polymer, [2] a syndiotactic dicyclopentadiene ring-opening polymer [3] a method for producing the syndiotactic dicyclopentadiene ring-opening polymer, and [4] a method for producing a hydrogenated syndiotactic crystalline dicyclopentadiene ring-opening polymer.

[1] A hydrogenated syndiotactic crystalline dicyclopentadiene ring-opening polymer having a melting point of lower than 280° C., an initial melting temperature of 260° C. or higher and a syndiotacticity of higher than 90%.

[2] A syndiotactic dicyclopentadiene ring-opening polymer, which can produce the hydrogenated syndiotactic crystalline dicyclopentadiene ring-opening polymer according to [1] by hydrogenation reaction, and has a syndiotacticity of higher than

[3] A method for producing the syndiotactic dicyclopentadiene ring-opening polymer according to [2], which includes a step of subjecting dicyclopentadiene to ring-opening polymerization using a polymerization catalyst including a tungsten compound represented by the following formula (1):

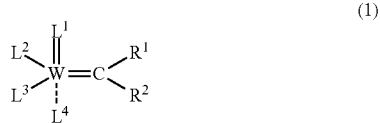

wherein W represents a tungsten atom;

each of $R^1$ and $R^2$ independently represents a group selected from a hydrogen atom, an alkyl group having 1 to 12 carbon atoms that may have a substituent, an aryl group having 6 to 12 carbon atoms that may have a substituent, and a cycloalkyl group having 3 to 20 carbon atoms that may have a substituent:

$L^1$ represents a nitrogen atom that may have a substituent selected from an alkyl group having, 1 to 12 carbon atoms that may have a substituent, an aryl group having 6 to 12 carbon atoms that may have a substituent, and a cycloalkyl group having 3 to 20 carbon atoms that may have a substituent, $L^2$ represents a conjugated heterocyclic group having 5 to 15-membered rings that includes at least one nitrogen atom, and the conjugated heterocyclic group may have a substituent;

$L^3$ represents an alkoxy group represented by O—$R^3$, where $R^3$ represents a group selected from an alkyl group having 1 to 12 carbon atoms that may have a substituent, and an aryl group having 6 to 30 carbon atoms that may have a substituent; and $L^4$ represents a neutral conjugated heterocyclic ligand having 12 to 24-membered rings that comprises at least two nitrogen atoms, where the conjugated heterocyclic ligand may have a substituent.

[4] A method for producing the hydrogenated syndiotactic crystalline dicyclopentadiene ring-opening polymer according to [1] including a step of subjecting, the syndiotactic dicyclopentadiene ring-opening polymer according to [2] to hydrogenation reaction.

In the present description, "may have a substituent" means "being unsubstituted or having a substituent".

Advantageous Effects of Invention

One aspect of the invention provides a hydrogenated syndiotactic crystalline dicyclopentadiene ring-opening polymer having a sufficiently high initial melting temperature, excellent heat resistance and advantageous industrial producibility, a syndiotactic dicyclopentadiene ring-opening polymer that is excellent in solution stability after polymerization reaction and can be converted into the hydrogenated product by hydrogenation reaction, and an efficient production method thereof.

DESCRIPTION OF EMBODIMENTS

The present invention provides a hydrogenated syndiotactic crystalline dicyclopentadiene ring-opening polymer having a melting point of lower than 280° C., an initial melting temperature of 260° C. or higher and a syndiotacticity of higher than 90% (hereinafter referred to as "hydrogenated crystalline dicyclopentadiene ring-opening polymer according to one embodiment of the invention" in some cases).

The hydrogenated crystalline dicyclopentadiene ring-opening polymer according to one embodiment of the invention includes repeating a unit of a hydrogenated poly(endo-dicyclopentadiene) represented by the following formula (2).

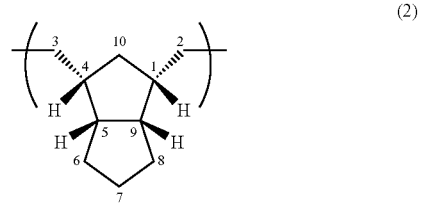

The initial melting temperature of the hydrogenated crystalline dicyclopentadiene ring-opening polymer according to one embodiment of the invention is 260° C. or higher. The upper limit of the initial melting temperature is not particularly limited, but is generally lower than 280° C., and equal to or lower than the melting point. Since the hydrogenated crystalline dicyclopentadiene ring-opening polymer according to one embodiment of the invention has a considerably high initial melting temperature, it has excellent processability such as solder reflow resistance.

The initial melting temperature in the present invention means an initial melting temperature (hereinafter referred to as "post-molten initial melting temperature" in some cases) determined after the hydrogenated crystalline dicyclopentadiene ring-opening polymer has been once sufficiently molten and then sufficiently crystallized. For example, this initial melting temperature can be measured in accordance with the method for measuring the post-molten initial melting temperature in Examples.

The melting point of the hydrogenated crystalline dicyclopentadiene ring-opening polymer according to one embodiment of the invention is lower than 280° C., and preferably 275° C. or lower. The lower limit of the melting point is not particularly limited, but is approximately 260° C., and equal to or higher than the initial melting temperature. The hydrogenated crystalline dicyclopentadiene ring-opening polymer according to one embodiment of the invention has a moderately high melting point, so that excellent heat resistance can be achieved, and oxidative degradation during forming can be reduced. On the other hand, if the melting point of the hydrogenated crystalline dicyclopentadiene ring-opening polymer is too high, it should be formed at a high temperature because of poor formability, and thus the hydrogenated crystalline dicyclopentadiene ring-opening polymer becomes susceptible to oxidative degradation.

The melting point in the present invention means a melting point (hereinafter referred to as "post-molten melting point" in some cases) determined after the hydrogenated crystalline dicyclopentadiene ring-opening polymer has been once sufficiently molten and then sufficiently crystallized. For example, this melting point can be measured in accordance with the method for measuring the post-molten melting point in Examples.

The hydrogenated crystalline dicyclopentadiene ring-opening polymer according to one embodiment of the invention has a tacticity, because the carbon represented by (1, 4) in the above formula (2) is an asymmetric carbon (indicated by *).

The hydrogenated crystalline dicyclopentadiene ring-opening polymer according to one embodiment of the invention is a polymer that has syndiotacticity, wherein the syndiotacticity i.e. a ratio of the racemo diads relative to the total amount of the meso diads and the racemo diads in the steric configuration ((hereinafter may be simply referred to as the ratio of the racemo diads in some cases) is higher than 90%.

When the ratio of the racemo diads is 90% or lower, the crystallinity of the hydrogenated syndiotactic crystalline dicyclopentadiene ring-opening polymer is greatly decreased, and the properties such as high initial melting temperature and processability are unpaired.

Specifically, the syndiotacticity can be determined by the formula I: [(racemo diads)/(meso diads+racemo diads)/100 (%)].

The ratio of the racemo diads can be calculated by analyzing $^{13}$C-NMR spectrum for the hydrogenated syndiotactic crystalline dicyclopentadiene ring-opening polymer. Specifically, the ratio can be determined by quantitatively measuring the spectrum of the carbon atoms indicated by (5, 9) in the above formula (2) of the hydrogenated syndiotactic crystalline dicyclopentadiene ring-opening polymer according to one embodiment of the invention. That is, the $^{13}$C-NMR spectrum measurement for the carbon atoms indicated by (5, 9) included in the repeating unit represented by the above formula (2) may be carried out in an o-dichlorobenzene-$d_4$/trichlorobenzene [mixing ratio (weight basis): 1/2] mixed solvent at 200° C., and a peak area value of the signal attributed to the meso diads at 43.35 ppm and a peak area value of the signal attributed to the racemo diads at 43.43 ppm are substituted into the above formula 1 to determine the ratio of the racemo diads.

The hydrogenated crystalline dicyclopentadiene ring-opening polymer and the syndiotactic dicyclopentadiene ring-opening polymer according to one embodiment of the invention have a repeating unit derived from dicyclopentadiene represented by the following formula (3).

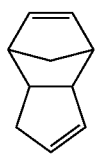

(3)

From the viewpoint that the syndiotactic dicyclopentadiene ring-opening polymer (hereinafter referred to as "dicyclopentadiene ring-opening polymer according to one embodiment of the invention" in some cases) and the hydrogenated crystalline dicyclopentadiene ring-opening polymer according to one embodiment of the invention particularly improve the heat resistance of the hydrogenated product and accelerate its crystallization rate thereof, it is preferable to use a polymer including a large number of dicyclopentadiene-derived repeating units. The ratio of the dicyclopentadiene-derived repeating units relative to all repeating units in the hydrogenated crystalline dicyclopentadiene ring-opening polymer and the dicyclopentadiene ring-opening polymer according to one embodiment of the invention is not particularly limited, but is preferably 90 wt % or higher, more preferably 95 wt % or higher, particularly preferably 97 wt % or higher, and most preferably the polymer consists only of the dicyclopentadiene-derived repeating units.

As mentioned below, the hydrogenated crystalline dicyclopentadiene ring-opening polymer according to one embodiment of the invention can be efficiently obtained by a process where dicyclopentadiene or a monomer mixture including dicyclopentadiene and other cycloolefin monomers (hereinafter whole of them is referred to as "dicyclopentadiene and the like" in some cases) is subjected to ring-opening polymerization in the presence of a specific ring-opening polymerization catalyst to obtain a dicyclopentadiene ring-opening polymer, which is then hydrogenated.

The dicyclopentadiene includes endo and exo stereoisomers, and both of them can be used as a monomer, either of which can be used alone, or a stereoisomer mixture including the endo and exo stereoisomers in any ratio can be used. From the viewpoint of increasing the crystallinity of the hydrogenated crystalline dicyclopentadiene ring-opening polymer and particularly improving its beat resistance, it is preferable to increase the ratio of one stereoisomer. The ratio of the endo or exo stereoisomer to be used is preferably 90% or higher, more preferably 95% or higher, and particularly preferably 99% or higher. Additionally, from the viewpoint of easiness of synthesis, it is preferable that the stereoisomer of which the ratio is increased, is the endo stereoisomer.

In the production of the dicyclopentadiene ring-opening polymer according to one embodiment of the invention, dicyclopentadiene may be used in combination with other cycloolefin monomers. The amount of other cycloolefin monomers to be used is preferably less than 10 wt %, more preferably less than 5 wt %, particularly preferably less than 3 wt %, and most preferably 0 wt % based on the total amount of dicyclopentadiene and other cycloolefin monomers.

Examples of other cycloolefin monomers that can be used in combination with dicyclopentadiene include the followings:

cycloalkenes such as cyclopentene, cyclohexene and cycloheptane; dicyclopentadienes such as tricyclo[4.3.1$^{2,5}$.0]dec-3-ene and tricyclo[4.4.1$^{2,5}$.0]undec-3-ene obtained by saturating the dicyclopentadiene or the double bond of the 5-membered ring moiety included in dicyclopentadiene;

norbornenes unsubstituted having an alkyl group as a substituent, such as norbornene, 5-methylnorbornene, 5-ethylnorbornene, 5-butylnorbornene, 5-hexylnorbornene, 5-decylnorbornene, 5-cyclohexyhiorbornene and 5-cyclopentyl iorbornene;

norbornenes having an alkenyl group as a substituent, such as 5-ethylidenenorbornane, 5-vinylnorbornene, 5-propenylnorbornene, 5-cyclohexenylnorboene and 5-cyclopentenyhiorbornene;

norbornenes having an aromatic ring as a substituent, such as 5-pbenylnorbornene;

norbornenes having an oxygen atom-containing polar group, such as 5-methoxycarbonylnorbornene, 5-ethoxycarbonylnorbornene, 5-methyl-5-methoxycarbonylnorbornene, 5-methyl-5-ethoxycarbonyhiorbornene, naibomenyl-2-methyl propionate, norbomenyl-2-methyl octanoate, norbornene-5,6-dicarbohe anhydride, 5-(hydroxymethyl)norbornene 5,6-di(hydroxyruethyl)norhomene 5,5-di(hydroxymethypnorbornene 5-hydroxy-i-propylnorbornene, 5,6-dicarboxynorbornene, and 5-methoxycarbonyl-6-carboxynorbornene; and norbornenes having a nitrogen atom-containing polar group, such as 5-cyanonorbornene and norbornene-5,6-dicarboxylic acid imide.

In addition, examples of tetracyclododecenes other than tetracyclododecene include the following: tetracyclododecenes having an alkyl group as a substituent, such as 8-methyltetracyclododecene. 8-ethyltetracyclododecene. 8-cyclohexyltetracyclododecene and 8-cyclopentyltetracyclododecene;

tetracyclododecenes having a double bond outside the ring, such as 8-methylidenetetracyclododecene, 8-ethylidenetetracyclododecene, 8-vinyltetracyclododecene. 8-propenyhetracyclododecene, 8-cyclohexemiltetracyclododecene, and 8-cyclopentenyltetracyelododecene;

tetracyclododecenes having an aromatic ring, such as 8-phenyltetracyclododecene;

tetracyclododeceries having an oxygen a om-containing substituent, such as 8-methoxycarbonyltetracyclododecene, 8-methyl-8-methoxycarbonyhetracyclododecene, 8-hydroxymethyltetracyclododecene, 8-carboxyletracyclododecene, tetracyclododecen-8,9-dicarboxylic acid, and tetracyclododecene-8,9-dicarboxylic anhydride;

tetracyclododecenes having a nitrogen atom-containing substituent, such as 8-cyanotetracyclododecene and tetracyclododecene-8,9-dicarboxylic acid imide;

tetracyclododecenes having a halogen atom-containing substituent, such as 8-chlorotetracyclododecene; and tetracyclododecenes having a silicon atom-containing substituent, such as 8-trimethoxysilyltetracyclododecene.

Examples of hexacycloheptadecenes include the followings: hexacycloheptadecenes unsubstituted or having an alkyl group as a substituent, such as hexacycloheptadecene, 12-methylhexacycloheptadecene, 12-ethylhexacycloheptadecene, 12-cyclohexylhexacycloheptadecene and 12-cyclopentylhexacycloheptadecene;

hexacycloheptadecenes having a double bond outside the ring, such as 12-methylidenehexacycloheptadecene, 12-ethylidenehexacycloheptadecerie, 12-vinylhexacycloheptadecene, 12-propenylhexacycloheptadecene, 12-cyclohexenylhexacycloheptadecene and 12-cyclopentenythexacycloheptadecene;

hexacycloheptadecenes having an aromatic ring as a substituent, such as 12-pberwlbexacyclobeptadecene;

hexacycloheptadecenes having an oxygen atom-containing substituent, such as 12-methoxycarbonylhexacycloheptadecene, 12-methyl-12-methoxycarbonylhexacycloheptadecene, 12-hydroxymethylhexacycloheptadecene, 12-caboxyhexacycloheptadecene, hexacycloheptadecene-12,13-dicarboxylic acid and hexacycloheptadecene-12,13-dicarboxylic anhydride;

hexacycloheptadecenes having a nitrogen atom-containing substituent, such as 12-evanohexacyclobeptadecene and hexacycloheptadecene-12,13-dicarboxylic acid imide;

hexacycloheptadecenes having a halogen atom-containing substituent, such as 12-chlorohexacycloheptadecene;

hexacycloheptadecenes having a silicon atom-containing substituent, such as 12-trimethoxvsilylhexacycloheptadecene; and tetracyclo[6.5.1$^{2,5}$.0$^{1,6}$.0$^{8,13}$]trideca-3,8,10,12-tetraene (also referred to as 1,4-methano-1,4,4a,9a-tetrahydrofluorene; tetracyclo[6.6.1$^{2,5}$.0$^{1,6}$.0$^{8,13}$]tetradeca-3,8,10,12-tetraene (also referred to as 4-methano-1,4,4a,5,10,10a-hexahydroanthracene); and the like.

The number average molecular weight (Mn) of the hydrogenated crystalline dicyclopentadiene ring-opening polymer according to one embodiment of the invention is normally 500 to 1,000,000, preferably 1000 to 600,000, more preferably 2.000 to 400,000. If the Mn is too low, the mechanical strength may be decreased, and if the Mn is too high, the polymer tends to be difficult to be formed. Note that the number average molecular weight of the hydrogenated syndiotactic crystalline dicyclopentadiene ring-opening polymer is approximately equal to that of the syndiotactic dicyclopentadiene ring-opening polymer before the hydrogenation process.

The glass transition temperature (Tg) of the hydrogenated crystalline dicyclopentadiene ling-opening polymer according to one embodiment of the invention is preferably 80° C. or higher, more preferably 85° C. or higher. If the glass transition temperature is within these ranges, the polymer is favorable because of improved heat resistance e.g. high deflection temperature under load. The upper limit of the glass transition temperature is not particularly limited, but is approximately 120° C.

The dicyclopentadiene ring-opening polymer according to one embodiment of the invention can be obtained by subjecting dicyclopentadiene and the like to ring-opening polymerization using a polymerization catalyst including a tungsten compound represented by the following formula (1).

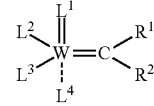

(1)

In the formula (1), W represents a tungsten atom.

Each of $R^1$ and $R^2$ independently represents a group selected from a hydrogen atom, an alkyl group having 1 to 12 carbon atoms that may have a substituent, an aryl group having 6 to 12 carbon atoms that may have a substituent, and a cycloalkyl group having 3 to 20 carbon atoms that may have a substituent.

$L^1$ represents a nitrogen atom that may have a substituent selected from an alkyl group having 1 to 12 carbon atoms that may have a substituent, an aryl group having 6 to 12 carbon atoms that may have a substituent and a cycloalkyl group having 3 to 20 carbon atoms that may have a substituent.

$L^2$ represents a conjugated heterocyclic group having at least one nitrogen atom and having 5 to 15-membered rings, where the conjugated heterocyclic group may have a substituent.

$L^3$ represents an alkoxy group represented by —O—$R^3$, where the $R^3$ represents a group selected from an alkyl group having 1 to 12 carbon atoms that may have a substituent and an aryl group having 6 to 30 carbon atoms that may have a substituent.

$L^4$ represents a neutral conjugated heterocyclic ligand having at least two nitrogen atoms and having 12 to 24-membered rings, where the conjugated heterocyclic ligand may have a substituent.

That is, in the production method according to one embodiment of the invention, the tungsten compound represented by the above formula (1) is used as a polymerization active component of a polymerization catalyst for ring-opening polymerization of die and the like.

In the above formula (1), W represents a tungsten atom.

Each of $R^1$ and $R^2$ independently represents a hydrogen atom; an alkyl group having 1 to 12 carbon atoms that may have a substituent, such as a methyl group, an ethyl group, a n-propyl group, an isopropyl group, a n-butyl group, an isobutyl group and a t-butyl group; a cycloalkyl group having 3 to 20 carbon atoms that may have a substituent, such as a cyclopropyl group, a cyclopentyl group, a cyclohexyl group; or an aryl group having 6 to 12 carbon atoms that may have a substituent. Examples of the aryl group of the aryl group that may have a substituent include a phenyl group, a 1-naphthyl group, a 2-naphthyl group and the like. In addition, examples of the substituent that may be included in the alkyl group having 1 to 12 carbon atoms, the cycloalkyl group having 3 to 20 carbon atoms and the aryl soup having 6 to 12 carbon atoms, include an alkyl group having 1 to 12 carbon atoms such as a methyl group and an ethyl group; a halogen atom such, as a fluorine atom, a chlorine atom and a bromine atom; an alkoxy group having 1 to 12 carbon atoms such as a methoxy group, a ethoxy group and an isopropoxy group; a haloalkyl group having 1 to 12 carbon atoms such as a trifluoromethyl group; a haloalkoxy group having 1 to 12 carbon atoms such as a trifluoromethoxy group; an aryl group having 6 to 12 carbon atoms that may have a substituent, such as a phenyl group, a 4-methylphenyl group, a 2,4-dimethylphenyl group, a 2-chlorophenyl group and a 3-methoxyphenyl group; and the like.

$L^1$ represents a nitrogen atom that may have a substituent selected from an alkyl group having 1 to 12 carbon atoms that may have a substituent, an aryl group having 6 to 12 carbon atoms that may have a substituent and a cycloalkyl group having. 3 to 2.0 carbon atoms that may have a substituent. That is, $L^1$ is a group represented by $=N-R^4$ ($R^4$ represents a hydrogen atom, or a group selected from an alkyl group having 1 to 12 carbon atoms that may have a substituent, an aryl group having 6 to 12 carbon atoms that may have a substituent, and a cycloalkyl group having 3 to 20 carbon atoms that may have a substituent).

The alkyl group having 1 to 12 carbon atoms of the substituent ($R^4$) that may be included in the nitrogen atom of the $L^1$ may be either linear or branched. Specific examples thereof include a methyl group, an ethyl group, a propyl group, an isopropyl group, a butyl group, a t-butyl group, a pentyl group, a hexyl group and the like.

Examples of the acyl group having 6 to 12 carbon atoms of the $R^4$ include a phenyl group, a 1-naphthyl group and a 2-naphthyl group and the like.

Examples of the cycloalkyl group having 3 to 20 carbon atoms of the $R^4$ include a cyclopropyl group, a cyclopentyl group, a cyclohexyl group, a cyclooctyl group, an adamantyl group and the like.

The substituent that may be included in the alkyl group having 1 to 12 carbon atoms, the cycloalkyl group having 3 to 20 carbon atoms, or the aryl group having 6 to 12 carbon atoms of the $R^4$, is not particularly limited.

Examples of the substituent that may be included in the alkyl group having 1 to 12 carbon atoms of the $R^4$ include a halogen atom such as a fluorine atom, a chlorine atom and a bromine atom; an alkoxy group having 1 to 12 carbon atoms such as a methoxy group, an ethoxy group and an isopropoxy group; an aryl group having, 6 to 12 carbon atoms that may have a substituent, such as a phenyl group, a 2-methylphenyl group, a 4-methylphenyl group, a 2,4-dimethylphenyl group, a 2-chlorophenyl group, a 3-methboxyphenyl group, a 2,6-dimethylphenyl group, a 3,5-dimethylphenyl group and a pentafluorophenyl group; an amino group; a monosubstituted amino group such as a methylamino group; a disubstituted amino group such as a dimethylamino group; an imino group: and the like.

Examples of the substituent that may be included in the cycloalkyl group having 3 to 20 carbon atoms or the aryl group having 6 to 12 carbon atoms of the $R^4$ include an alkyl group having 1 to 12 carbon atoms such as a methyl group, an ethyl group and an isopropyl group; a halogen atone such as a fluorine atom, a chlorine atom and a bromine atom; an alkoxy group having 1 to 12 carbon atoms such as a methoxy group, ethoxy group and an isopropoxy group, a haloalkyl group having 1 to 12 carbon atoms such as a trifluoromethyl group; a haloalkoxy group having 1 to 12 carbon atoms such as a trifluoromethoxy group; an aryl group having 6 to 12 carbon atoms that may have a substituent, such as a phenyl group, a 2-methylphenyl group, a 4-methylphenyl group, a 2,4-dimethylphenyl group, a 2-chlorophenyl group, a 3-methboxyphenyl group, a 2,6-dimethylphenyl group a 3,5-dimethylphenyl group and a pentafluorophenyl group; an amino group; a monosubstituted amino group such as a methylamino group; a disubstituted amino group such as a dimethylamino group; an imino group; and the like.

$L^2$ represents a conjugated heterocyclic group having at least one nitrogen atom and having 5 to 15-membered rings, that may have a substituent, Examples of the corrugated heterocyclic group of $L^2$ include a 5-membered ring conjugated heterocyclic group such as a pyrrolyl group, an imidazolyl group, a pyrazolyl group, an oxazolyl group, and a thiazolyl group; a 6-membered ring conjugated heterocyclic croup such as a pyridyl group, a pyridazinyl group, a pyrimidinyl group, a pyrazinyl group and a triazinyl group; a fused ring conjugated heterocyclic group such as a quinazolinyl group, a phthalazinyl group and a pyrrolopyridyl group; and the like.

The substituent that may be included in the conjugated heterocyclic group is not particularly limited. Its examples include an alkyl group having 1 to 12 carbon atoms such as a methyl group and an ethyl group; a halogen atom such as a fluorine atom, a chlorine atom and a bromine atom; an alkoxy group having 1 to 12 carbon atoms such as a methoxy group, an ethoxy group and an isopropoxy group; a haloalkyl group having 1 to 12 carbon atoms such as a trifluoromethyl group; a haloalkoxy group having 1 to 12 carbon atoms such as a trifluoromethoxy group; a aryl group having 6 to 12 carbon atoms that may have a substituent, such as a phenyl group, a 4-methylphenyl group, a 2,4-dimethylphenyl group, a 2-chlorophenyl group and a 3-methoxyphenyl group; an amino group; a monosubstituted amino group such as a methylamino group; a disubstituted amino group such as a dimethylamino group; an imino group; and the like.

$L^3$ is an alkoxy group represented by $-O-R^3$. $R^3$ is a group selected from an alkyl group having 1 to 12 carbon atoms that may have a substituent and an aryl group having 6 to 30 carbon atoms that may have a substituent.

Examples of the alkyl group having 1 to 12 carbon atoms among the alkyl group having 1 to 12 carbon atoms that may have a substituent of the $R^3$, include a methyl group, an ethyl group, a propyl group, an isopropyl group, a butyl group, a t-butyl group, a pentyl group and the like.

The substituent that may be included in the alkyl group having 1 to 12 carbon atoms of the $R^3$ is not particularly limited. Its examples include a halogen atom such as a fluorine atom, a chlorine atom and a bromine atom; an alkoxy group having 1 to 12 carbon atoms such as a methoxy group, an ethoxy group and an isopropoxy group; a haloalkyl group having 1 to 12 carbon atoms such as a trifluoromethyl group; a haloalkoxy group having 1 to 12 carbon atoms such as a trifluoromethoxy group; an aryl group having 6 to 12 carbon atoms that may have a substituent, such as a phenyl group, a 4-methylphenyl group, a 24-dimethylphenyl group, a 2-chlorophenyl group and a 3-methoxyphenyl group; an amino group; a monosubstituted amino group such as a methylamino group; a disubstituted amino group such as a dimethylamino group; an group; and the like.

Examples of the aryl group having 6 to 30 carbon atoms among the aryl group having 6 to 30 carbon atoms that may have a substituent, include a phenyl group, a 1-naphthyl group, a 2-naphthyl group, an adamantyl group and the like.

The substituent that may be included in the aryl group having 6 to 30 carbon atoms of the $R^3$ is not particularly limited Its examples include a halogen atom such as a fluorine atom, a chlorine atom and a bromine atom; an alkyl group having 1 to 12 carbon atoms such as a methyl group, an ethyl group, an isopropyl group and a t-butyl group; a cycloalkyl group having 3 to 20 carbon atones such as a cyclopropyl group, a cyclopentyl group and a cyclohexyl group; an alkoxy group having 1 to 12 carbon atoms such as a methoxy group, an ethoxy group and an isopropoxy group; a haloalkyl group having 1 to 12 carbon atoms such as a trifluoromethyl group; a haloalkoxy group having 1 to 12 carbon atoms such as a trifluoromethoxy group; an aryl group having 6 to 12 carbon atoms that may have a substituent, such as a phenyl group, a 4-methylphenyl group, a 2,4-dimethylphenyl group, a 2-chlorophenyl group and a 3-methoxyphenyl group; an amino group; a monosubstituted amino group such as a methylamino group; a disubstituted amino group such as a dimethylamino group; an imino group; and the like.

Specific examples of the $L^3$ include a group that is an alkyl group having 1 to 12 carbon atoms in which $R^3$ may have a substituent, such as a 1,1,1,3,3,3-hexafluoro-2-propoxy group, a 2-methyl-2-propoxy group, a 1,1,1-trifluoro-2-methyl-2-propoxy group, a 1,1,1-trifluoro-2-trifluoromethyl-2-propoxy group and a 2-trifluoromethyl-2-phenyl-1,1,1-trifluoroethoxy group; and a group that is an aryl group having 6 to 30 carbon atoms in which $R^3$ may have a substituent, such as a 2,6-bis(2,4,6-trimethylphenyl)phenoxy group, a 2,6-bis(2,4,6-triisopropylphenyl)phenoxy group, a 2,4,6-trimethylphenoxy group and a 2,3,5,6-tetraphenylphenoxy group.

$L^4$ is a neutral conjugated heterocyclic ligand having at least two nitrogen is atoms and having 12 to 24-membered rings. Specific examples of the ligand include 2,2'-bipyridyl, 5,5'-dimethyl-2,2'-bipyridyl, 4,4'-dimethyl-2,2'-bipyridyl, 4,4'-dibromo-2,2'-bipyridyl, 2,2'-biquinoline, 1,10-phenanthroline and terpyridine.

In addition, the conjugated heterocyclic, group of the $L^4$ may have a substituent. Examples of the substituent include the same substituents as listed as the substituents that may be included in the conjugated heterocyclic group of the $L^2$.

Specific examples of the tungsten compound used in the present invention include, but are not limited to, (2-trifluoromethyl-2-phenyl-1,1,1-trifluoroethoxy)2,6-diisopropylphenylimide tungsten (VI) (2,5-dimethylpyrrolide) (neophylidene) (1,10-phenanthroline), (2-trifluoromethyl-2-phenyl-1,1,1-trifluomethoxy)-2,6-diisopropylphenylimide tungsten (VI) (2,5-dimethylpyrrolide) (neophylidene) (2,2'-bipridine), and the like.

In addition, the tungsten compound used as a polymerization catalyst has a neutral conjugated heterocyclic ligand, and may be used in combination with a metal salt compound for increasing the rate of the ring-opening polymerization of dicyclopentadiene. By combining a metal salt compound, the neutral conjugated heterocyclic ligand can be separated from the tungsten compound to form highly active catalyst species.

As the metal atom constituting, the metal salt, zinc, tin, copper, titanium, rare earth and the like are suitable. Specific examples of the metal salt that may be used include zinc chloride, copper chloride, tin chloride, titanium chloride, scandium chloride, yttrium chloride and the like.

These tungsten compounds can be produced e.g. in accordance with the method described in JP-T-2014-520103 (WO 2012/167171) or the like. Further, those commercially available as tungsten compounds can be purified and used as desired.

In the method for producing the dicyclopentadiene ring-opening polymer according to one embodiment of the invention, dicyclopentadiene or the like and a polymerization catalyst may be mixed for ring-opening polymerization of dicyclopentadiene or the like.

Although the amount of the polymerization catalyst to be used relative to dicyclopentadiene and the like is not particularly limited, the molar ratio of tungsten compound in the polymerization catalyst: dicyclopentadiene and the like is preferably 1:10 to 1:2,000,000, more preferably 1:200 to 1:1,000,000, and particularly preferably 1:500 to 1:500,000. If the amount of the polymerization catalyst to be used is too large, it may be difficult to remove the polymerization catalyst, and if the amount of the polymerization catalyst to be used is too small, sufficient polymerization activity may not be obtained, The polymerization reaction may be effected in a solvent-fine system, but preferably in an organic solvent from the viewpoint that the reaction can be advantageously controlled. The organic solvent used in this case is not particularly limited as long as the organic solvent can dissolve or disperse the resulting ring-opening polymer and does not adversely affect the polymerization reaction. Specific examples of the organic solvent that may be used include an aliphatic hydrocarbon such as pentane, hexane and heptane alicyclic hydrocarbon such as cyclopentane, cyclohexane, methylcyclohexane, dimethylcyclohexane, trimethylcyclohexane, ethylcyclohexune, diethylcyclohexane, decahydronaphthalene, bicycloheptane, tricyclodecane, hexahydroindenecyclohexane and cyclooctane, an aromatic hydrocarbon such as benzene, toluene and xylene; a halogen-containing aliphatic hydrocarbon such as dichloromethane, chloroform and 1,2-dichloroethane; a halogen-containing aromatic hydrocarbon such as chlorobenzene and dichlorobenzene; a nitrogen-containing hydrocarbon such as nitromethane, nitrobenzene and acetonitrile; an ether such as diethyl ether and tetrahydrofuran; an aromatic ether such as anisole and phenetole; and the like. Among them, an aromatic hydrocarbon, an aliphatic hydrocarbon, an alicyclic hydrocarbon, an ether, and an aromatic ether are preferably used When effecting the polymerization reaction in the organic solvent, the concentration of the monomer in the reaction system is not particularly limited, but is preferably 1 to 50 wt %, more preferably 2 to 45 wt %, and particularly preferably 3 to 40 wt %. If the concentration of the monomer is too low, productivity may decrease, and if the concentration of the monomer is too high, the viscosity of the reaction solution may increase to a too large extent after completion of the polymerization reaction, and it may be difficult to effect the subsequent hydrogenation reaction.

The polymerization temperature is not particularly limited, but is normally −30 to +200° C., and preferably 0 to 180° C. Further, the polymerization time is also not particularly limited but is normally selected within the range of 1 minute to 100 hours. [0061]

When effecting the polymerization reaction, a vinyl compound or a diene compound may be added to the polymerization reaction system in order to adjust the molecular weight of the resulting dicyclopentadiene ring-opening polymer.

The vinyl compound used for adjusting the molecular weight is not particularly limited as long as the vinyl compound is an organic compound having a vinyl group. For example, α-olefins such as 1-butene, 1-pentene, 1-hexene and 1-octene; styrenes such as styrene and vinyltoluene; ethers such as ethyl vinyl ether, vinyl ether and ally glycidyl ether; a halogen-containing vinyl compound such as ally chloride; an oxygen-containing vinyl compound such as allyl acetate, allyl alcohol and glycidyl methacrylate; a nitrogen-containing vinyl compound such as acrylamide; silicon-containing vinyl compound such as vinyltrimethylsilane, allyltrimethylsilane and vinyltrimethoxysilane; and the like can be used.

Further, the diene compound used for adjusting the molecular weight is not particularly limited. For example, a non-conjugated diene such as 1,4-pentadiene, 1,4-hexadiene, 1,5-hexadiene, 1,6-heptadiene, 2-methyl-1,4-pentadiene and 2,5-dimethyl-1,5-hexadiene; a conjugated diene such as 1,3-butadiene, 2-methyl-1,3-butadiene, 1,3-dimethyl-1,3-butadiene, 1,3-pentadiene and 1,3-hexadiene; and the like can be used.

The amount of the added vinyl compound or diene compound may be determined depending on the intended molecular weight, but is normally selected within a range of 0.1 to 10 mol based on 100 mol of the dicyclopentadiene and the like used as the monomer.

In the present invention, the ring-opening polymerization reaction of dicyclopentadiene can be effected under the above-mentioned conditions using a polymerization catalyst including the tungsten compound represented by the above formula (1) to obtain a dicyclopentadiene ring-opening polymer having syndiotacticity.

In addition, the dicyclopentadiene ring-opening polymer having this syndiotactic structure can be subjected to hydrogenation reaction to obtain a hydrogenated syndiotactic crystalline dicyclopentadiene ring-opening polymer having syndiotacticity as well as crystallinity.

Note that the dicyclopentadiene ring-opening polymer may be collected from the reaction solution, and then subjected to the hydrogenation reaction, or the reaction solution including the dicyclopentadiene ring-opening polymer may be subjected directly to the hydrogenation reaction.

The number average molecular weight (Mn) of the dicyclopentadiene ring-opening polymer according to one embodiment of the invention to be subjected to the hydrogenation reaction determined by $^1$-HMR is not particularly hmited, but is preferably 1,000 to 1,000,000, and more preferably 2,000 to 800,000. A hydrogenated syndiotactic crystalline dicyclopentadiene ring-opening polymer that exhibits particularly an excellent balance between forming processability and heat resistance, can be obtained by subjecting dicyclopentadiene ring-opening polymer having such a number average molecular weight to hydrogenation reaction. The number average molecular weight of the hydrogenated syndiotactic crystalline dicyclopentadiene ring-opening polymer can be regulated by adjusting the addition amount or the like of the molecular weight modifier to be used in polymerization.

The cis content in the dicyclopentadiene ring-opening polymer according to one embodiment of the invention to be subjected to the hydrogenation reaction determined by $^1$H-NMR is preferably higher than 50%, and more preferably higher than 70%.

In the dicyclopentadiene ring-opening polymer according to one embodiment of the invention, the ratio of the racemo diads is preferably higher than 90%. When the cis content is higher than 50% and the ratio of the racemo diads is higher than 90%, the solubility of the dicyclopentadiene ring-opening polymer in an organic solvent increases, and the production process for directly subjecting the reaction solution containing the dicyclopentadiene ring-opening polymer to hydrogenation reaction is advantageous, and thus the ratio is preferable.

As described above, the syndiotactic dicyclopentadiene ring-opening polymer according to one embodiment of the invention that may be used as an intermediate of the hydrogenated syndiotactic crystalline dicyclopentadiene ring-opening polymer according to one embodiment of the invention, dissolves in an organic solvent at room temperature. In particular, from the viewpoint of the production process in which the polymerization reaction is carried out in an organic solvent and the organic solvent reaction solution containing the dicyclopentadiene ring-opening polymer is directly subjected to the hydrogenation reaction, it is preferable to dissolve the polymer in an organic solvent inert to hydrogenation.

Examples of the solvent for dissolving the dicyclopentadiene ring-opening polymer according to one embodiment of the invention include an alicyclic hydrocarbon such as cyclopentane, cyclohexane, methylcyclohexane, dimethylcyclohexane, trimethylcyclohexane, ethylcyclohexane, diethylcyclohexane, decahydronaphthalene, bicycloheptane, tricyclodecane, hexahydroindenecyclohexane and cyclooctane; an aromatic hydrocarbon such as benzene, toluene and xylene; a halogen-containing aliphatic hydrocarbon such as dichloromethane, chloroform and 1,2-dichloroethane; a halogen-containing aromatic hydrocarbon such as chlorobenzene and dichlorobenzene; an ether such as diethyl ether and tetrahydrofuran; an aromatic ether such as anisole and phenetole; and the like.

In the method for producing the hydrogenated crystalline dicyclopentadiene ring-opening polymer according to one embodiment of the invention, the hydrogenated syndiotactic crystalline dicyclopentadiene ring-opening polymer is obtained by a process (a) in which a hydrogenating agent is added to a system including the dicyclopentadiene ring-opening polymer obtained as above, then heated and reacted, or a process (b) in which a hydrogenation catalyst is added to the system, to which hydrogen is then added to hydrogenate the carbon-carbon double bond included in the dicyclopentadiene ring-opening polymer. Among them, from the viewpoint of industrial production, the process (b) in which the hydrogenation is carried out using the hydrogenation catalyst and the hydrogen gas, is preferable.

When conducting the method for producing the hydrogenated crystalline dicyclopentadiene ring-opening polymer according to one embodiment of the invention, in the process (a), it is preferable that a hydrazine-containing compound as a hydrogenating, agent for a transfer hydrogenation is used to hydrogenate the carbon-carbon double bond included in the dicyclopentadiene ring-opening polymer.

The compound used as a hydrogenating agent for a transfer hydrogenation is not particularly limited. The compound used as a hydrogenating agent for the dicyclopentadiene ring-opening polymer may be a compound used as a hydrogenation catalyst. Specific examples of the hydrogenating agent include hydrazine, paratoluenesulfonyl hydrazide and the like.

In the present invention, for the hydrogenation catalyst used in the process (b), a conventionally known catalyst can be used as a hydrogenation catalyst for ring-opening polymers. Specific examples of the catalyst include $RuHCl(CO)(PPh_3)_3$, $RuHCl(CO)[P(p-Me-Ph)_3]_3$, $RuHCl(CO)(PCy_3)_2$, $RuHCl(CO)[P(n-Bu)_3]_3$, $RuHCl(CO)[P(i-Pr)_3]_2$, $RuH_2(CO)[P(p-Me-Ph)_3]_3$, $RuH_2(CO)(PCy_3)_3$, $RuH_2(CO)[P(n-Bu)_3]_3$ $RuH(OCOCH_3)(CO)(PPh_3)_2$, $RuH(OCOPh)(CO)(PPh_3)_2$, $RuH(OCOPh-CH_3)(CO)(PPh_3)_2$, $RuH(OCOPh-OCH_3)(CO)(PPh_3)_2$, $RuH(OCOPh)(CO)(PCy_3)_2$, Raney nickel, nickel diatomaceous earth, nickel acetate, palladium acetate, $PdCl_2$, $RhCl(PPh_3)_3$, and the like.

The hydrogenation reaction is normally effected in an inert organic solvent. Examples of the inert organic solvent that may be used include an alicyclic hydrocarbon such as cyclopentane, cyclohexane, methyleyclohemine, dimethylcyclohexane, trimethylcyclohexane, ethylcyclohexane, diethylcyclohexane, decahydronaphthalene, bicycloheptane, tricyclodecane, hexahydroindenecyclohexane and cyclooctane: an aromatic hydrocarbon such as benzene, toluene and xylene; a halogen-containing aliphatic hydrocarbon such as dichloromethane, chloroform and 1,2-dichloroethane; a halogen-containing aromatic hydrocarbon such as chlorobenzene and dichlorobenzene; an ether such as diethyl ether and tetrahydrofuran; an aromatic ether such as anisole and phenetole: and the like.

In the method for producing the hydrogenated crystalline dicyclopentadiene ring-opening polymer according to one embodiment of the invention, preferably hydrogen is further added to a system including a dicyclopentadiene ring-opening polymer and a hydrogenation catalyst to hydrogenate the carbon-carbon double bond included in the dicyclopentadiene ring-opening polymer.

The hydrogenation reaction may also be effected under different conditions depending on the hydrogenation catalyst system to be used, but the reaction temperature is normally −20 to +250° C., preferably −10 to +220° C. and more preferably 0 to +200° C. If the hydrogenation temperature is too low, the reaction rate may become too slow. If the hydrogenation temperature is too high, a side reaction may occur. In a case of catalytic hydrogenation, the hydrogen pressure is normally set to 0.01 to 20 MPa, preferably 0.05 to 15 MPa, and more preferably 0.1 to 10 MPa. If the hydrogen pressure is too low, the hydrogenation rate may become too slow. If the hydrogen pressure is too high, a reactor that can endure high pressure, is necessary, and in this respect, restriction of the apparatus is caused. The reaction time is not particularly limited as long as the hydrogenation rate is suitable as desired, but is normally 0.1 to 10 hours. After completion of the hydrogenation reaction, the desired hydrogenated syndiotactic crystalline dicyclopentadiene ring-opening polymer may be simply collected using an ordinary method. When collecting the polymer, the residual catalyst may be removed by filtration or the like.

The hydrogenation ratio of the hydrogenated crystalline dicyclopentadiene ring-opening polymer according to one embodiment of the invention achieved by the hydrogenation reaction of the dicyclopentadiene ring-opening polymer (the ratio of the hydrogenated main-chain double bonds) is not particularly limited, but is preferably 98% or higher, and more preferably 99% or higher. The resulting hydrogenated syndiotactic crystalline dicyclopentadiene ring-opening polymer exhibits better heat resistance, as the hydrogenation ratio increases.

In addition, the tacticity of the hydrogenated syndiotactic crystalline dicyclopentadiene ring-opening polymer according to one embodiment of the invention is not particularly limited as long as the hydrogenated product has crystallinity and is syndiotactic (the ratio of the racemo diads is higher than 90%).

The hydrogenated syndiotactic crystalline dicyclopentadiene ring-opening polymer obtained by the production method according to one embodiment of the invention has a high initial melting temperature. Thus, this hydrogenated syndiotactic crystalline dicyclopentadiene ring-opening polymer may exhibit excellent heat resistance even after formed by melt forming, and it can be particularly advantageously used as a material of a formed article requiring heat resistance. The formed article can be produced according to a known method.

Examples of the applications of the formed article include, but are not limited to, an optical reflector, an insulating material, an optical film, a connector, a food packaging material, a bottle, a pipe, a gear, fibers a nonwoven fabric, and the hie.

EXAMPLES

Next, the invention will be further described below by way of examples, but the invention is not limited to the following examples.

Note that the following measurement methods and evaluation methods were used in connection with the examples.
(1) Number Average Molecular Weight of Dicyclopentadiene Ring-Opening Polymer The ratio of the number of hydrogen atoms present at the terminals of the polymer chain to the number of hydrogen atoms present in the polymer chain excluding the terminals was calculated based on the $^1$H-NMR measurement results, and the number average molecular weight of the dicyclopentadiene ring-opening polymer was calculated based on the calculated ratio.
(2) Cis/Trans Content in Dicyclopentadiene Ring-Opening Polymer Determination was carried out based on the $^1$H-NMR measurement results.
(3) Hydrogenation Ratio of Hydrogenated Syndiotactic Crystalline Dicyclopentadiene Ring-Opening Polymer Determination was carried out based on the $^1$H-NMR measurement results.
(4) Melting Point and Initial Melting Temperature of Hydrogenated Syndiotactic Crystalline Dicyclopentadiene Ring-Opening Polymer The temperatures were measured using a differential scanning calorimeter while heating the polymer at a rate of 10° C./minute. A temperature at which the endothermic (crystal melting) heat flow was a maximum at an endothermic peak due to phase transition observed in the measurement with rising temperature, was defined as the melting point, and an intersection of a tangent before the endothermic (crystal melting) heat flow of the endothermic peak due to the phase transition was maxi rum and a baseline, was: a temperature at which the material began to melt, and the intersection was defined as an initial melting temperature, so that the melting point and the initial melting temperature were determined.

Note that the post-molten melting point and the post-molten initial melting temperature were measured by a process in which the hydrogenated syndiotactic crystalline dicyclopentadiene ring-opening polymer was molten by heating at 320° C. for 10 minutes and subsequently cooled to room temperature at 10° C./minute to crystallize it, and then subjected to measurement by using a differential scanning calorimeter while heating at 10° C./minute, as described below.

(5) Ratio of Racemo Diads in Hydrogenated Syndiotactic Crystalline Dicyclopentadiene Ring-Opening Polymer $^{13}$C-NMR measurement at 200° C. was carried out using o-dichlorobenzene-d$_4$/trichlorobenzene (mixing ratio (weight basis): 1/2) as a solvent, and the ratio of the racemo diads was determined based on the a peak area value of the signal at 43.35 ppm attributed to the meso diads and a peak area value of the signal at 43.43 ppm attributed to the racemo diads.

(6) Solder Immersion Test of Hydrogenated Syndiotactic Crystalline Dicyclopentadiene Ring-Opening Polymer The hydrogenated syndiotactic crystalline dicyclopentadiene ring-opening polymer as a sample was molten by heating at 320° C. for 10 minutes, formed into a shape of 10 mm=100 mm=1 mm and then cooled to room temperature at a rate of 10° C./minute, and the resulting sample piece was immersed in solder at 260° C. for 20 seconds, and the presence or absence of deformation was evaluated in accordance with the following criteria. A case without visible deformation can be evaluated as "excellent in heat resistance".

[Evaluation Criteria]
"Good": No visible deformation
"Bad": Visible deformation (7) Curling Value of Hydrogenated Syndiotactic Crystalline Dicyclopentadiene Ring-Opening Polymer One end of the sample piece subjected to the solder immersion test was placed on a horizontal plane, and the distance between the other end in the longitudinal direction of the sample piece and the horizontal plane gas measured, and the measured slue was defined as a curling value. It was determined tint the sample piece exhibited better heat resistance as the curling value decreased.

Synthesis Example 1

Synthesis of Catalyst (A)

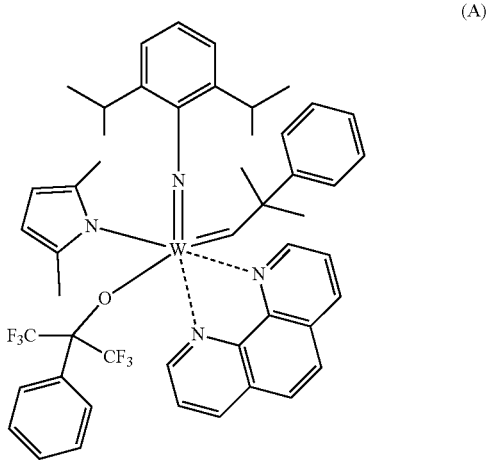

(A)

As a bispyrrolide precursor, 337 mg (0.5 mmol) of W(CHCMe$_2$Ph) (NAr$^{diiPr}$) (Me$_2$Pyr)$_2$ (wherein Me represents a methyl group, Ph represents a phenyl group, Ar$^{diiPr}$ represents a 2,6-diisopropylphenyl group, and Me$_2$Pyr represents 2,5-dimethylpyrrole) was dissolved in 5 ml of benzene, to which 84 μl (0.5 mmol) of α,α-bistrifluoromethylbenzyl alcohol [Ph(CF$_3$)$_2$COH] was added, and the whole content (reaction mixture) was stirred at room temperature (20° C.) for 2 hours. Then, 90 mg (0.5 mmol) of 1,10-phenanthroline was added the whole content was stirred at room temperature (20° C.) for 1 hour, and then the reaction mixture was transferred into a freezer. 10 ml of pentane was added to the reaction mixture to quantitatively precipitate the reaction product. The reaction product was taken by filtration as an orange solid. This product was washed with pentane and dried. The yield was 490 mg (quantitatively).

This product was identified as (2-trifluoromethyl-2-phenyl-1,1,1-trifluoroethoxy)-2,6-diisopropylphenylimde tungsten (VI) (2,5-dimethylpyrrolide) (neophylidene) (1,10-phenanthroline) by $^1$H-NMR, $^{13}$C-NMR and $^{19}$F-NMR spectra of the resulting solid.

Example 1

A glass reactor equipped with a stirrer was charged with 0.076 g of (2-trifluoromethyl-2-phenyl-1,1,1-trifluoroethoxy)-2,6-diisopropylphenylimide tungsten(VI)(2,5-dimethylpyrrolide) (neophylidene) (1,10-phenanthroline) obtained in Synthesis Example 1 and 1 g of toluene, to which 5.0 g of dicyclopentadiene 20.0 g cyclohexane and 0.21 g of 1-hexene were subsequently added, and furthermore 0.0105 g of anhydrous zinc chloride dissolved in 5 g of 1,4-dioxane was added, which was subjected to polymerization reaction at 50° C. After the start of the polymerization reaction, a white turbidness of 1,10-phenanthroline zinc was rapidly produced. After 3-hour reaction, a large quantity of acetone was poured into the polymerization reaction solution to aggregate a precipitate, the aggregate was filtered off, washed, and then dried under reduced pressure at 40° C. for 24 hours. A dicyclopentadiene ring-opening polymer obtained had a yield of 4.3 g, had a number average molecular weight of 10,900, and a cis content of 81%.

Subsequently, a glass reactor equipped with a stirrer was charged with 2.5 g the resulting dicyclopentadiene ring-opening polymer and 21 g of para toluenesulfonyl hydrazide were added, to which 500 ml of p-xylene was added, and hydrogenated at 125° C. for 5 hours. This hydrogenation reaction solution was poured into a large quantity of methanol to completely precipitate the resulting hydrogenated dicyclopentadiene ring-opening polymer, which was filtered off, washed, and then dried under reduced pressure at 40° C. for 24 hours.

The hydrogenation ratio of the resulting hydrogenated dicyclopentadiene ring-opening polymer was 99% or higher, and the ratio of the racemo diads was 91%. In addition, the melting point of the hydrogenated dicyclopentadiene ring-opening polymer dried under reduced pressure, directly measured as a sample, was 277° C., and its melting enthalpy was 35 Jig.

On the other hand, the hydrogenated dicyclopentadiene ring-opening polymer dried under reduced pressure was heated at 320° C. for 10 minutes to sufficiently melt it, then cooled to room temperature at a rate of 10° C./minute and sufficiently crystallized, and the melting point (post-molten melting point) of the resulting product, measured as a sample (hereinafter referred to as "post-molten sample" in some cases), was 275° C., and its melting enthalpy was 29

J/g. Further, at this time, the initial melting temperature (post-molten initial melting temperature) was 264° C., For this post-molten sample, the solder immersion test and the curling value measurement were carried out. The results are shown in Table 1.

Example 2

In an autoclave equipped with a stirrer, 1.75 g of the dicyclopentadiene ring-opening polymer obtained in Example 1 and 47 g of cyclohexane were added. Then, a solution in which 0.00157 g of RuHCl(CO)(PPh$_3$)$_3$ was dispersed in 10 ml of cyclohexane was further added and a hydrogenation reaction was carried out under a hydrogen pressure of 4.0 MPa at 160° C. for 8 hours. The hydrogenated dicyclopentadiene ring-opening polymer produced by pouring this hydrogenation reaction solution into a large amount of acetone was completely precipitated, filtered out, washed, and then dried under reduced pressure at 40° C. for 24 hours.

The hydrogenation ratio of the resulting hydrogenated dicyclopentadiene ring-opening polymer was 99% or higher, and the ratio of the racemo diads was 91%. In addition, the melting point of the hydrogenated dicyclopentadiene ring-opening polymer dried under reduced pressure, directly measured as a sample was 278° C., and its melting enthalpy was 40 J/g.

On the other hand, the post-molten sample obtained in the same way as in Example 1 had a melting point (post-molten melting, point) of 274° C. and a melting enthalpy of 28 J/g. Further, at this time, the initial melting temperature (post-molten initial melting temperature) was 265° C.

For this post-molten sample, the solder immersion test and the curling value measurement were carried out. The results are shown in Table 1.

TABLE 1

|  | Example | |
| --- | --- | --- |
|  | 1 | 2 |
| Post-molten melting point (° C.) | 275 | 774 |
| Post-molten initial melting temperature (° C.) | 264 | 265 |
| Solder immersion test | Good | Good |
| Curling value (mm) | 0 | 0 |

As is apparent from Table 1, the hydrogenated syndiotactic crystalline dicyclopentadiene ring-opening polymer according to one embodiment of the invention was proved to be a material that had a high initial melting temperature (post-molten initial melting temperature) and excellent heat resistance, not thermally deformed even if brought into contact with solder, and allowed implementation of solder reflow and the like (Examples 1 and 2).

Consequently, according to the present invention, a hydrogenated syndiotactic crystalline dicyclopentadiene ring-opening polymer that has a high initial melting temperature and excellent heat resistance after melting and is not thermally deformed even if brought into contact with solder, can be obtained.

The invention claimed is:

1. A hydrogenated syndiotactic crystalline dicyclopentadiene ring-opening polymer having a melting point of lower than 280° C., an initial melting temperature of 264° C. or higher and a syndiotacticity of higher than 90%,
   wherein the hydrogenated syndiotactic crystalline dicyclopentadiene ring-opening polymer comprises repeating units derived from a dicyclopentadiene either at a ratio of endo stereoisomer of 90% or more or at a ratio of exo stereoisomer of 90% or more.

2. A syndiotactic dicyclopentadiene ring-opening polymer, which can produce the hydrogenated syndiotactic crystalline dicyclopentadiene ring-opening polymer according to claim 1 by hydrogenation reaction and has a syndiotacticity of higher than 90%.

3. A method for producing the syndiotactic dicyclopentadiene ring-opening polymer according to claim 2, which includes a step of subjecting dicyclopentadiene to ring-opening polymerization using a polymerization catalyst comprising a tungsten compound represented by the following formula (1):

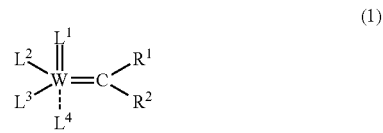

(1)

wherein W represents a tungsten atom;
each of $R^1$ and $R^2$ independently represents a group selected from a hydrogen atom, an alkyl group having 1 to 12 carbon atoms that may have a substituent, an aryl group having 6 to 12 carbon atoms that may have a substituent, and a cycloalkyl group having 3 to 20 carbon atoms that may have a substituent;
$L^1$ represents a nitrogen atom that may have a substituent, selected from an alkyl group having 1 to 12 carbon atoms that may have a substituent, an aryl group having 6 to 12 carbon atoms that may have a substituent, and a cycloalkyl group having 3 to 20 carbon atoms that may have a substituent;
$L^2$ represents a conjugated heterocyclic group having 5 to 15-membered rings that comprises at least one nitrogen atom, wherein the conjugated heterocyclic group may have a substituent;
$L^3$ represents an alkoxy group represented by O—$R^3$, wherein $R^3$ represents a group selected from an alkyl group having 1 to 12 carbon atoms that may have a substituent, and an aryl group having 6 to 30 carbon atoms that may have a substituent; and
$L^4$ represents a neutral conjugated heterocyclic ligand having 12 to 24-membered rings that comprises at least two nitrogen atoms, wherein the conjugated heterocyclic ligand may have a substituent.

4. A method for producing the hydrogenated syndiotactic crystalline dicyclopentadiene ring-opening polymer according to claim 1 including a step of subjecting the syndiotactic dicyclopentadiene ring-opening polymer according to claim 2 to hydrogenation reaction.

* * * * *